United States Patent [19]

Jaecker

[11] Patent Number: 4,743,575

[45] Date of Patent: May 10, 1988

[54] PREPARATIVE PROCESS FOR METHANE CONVERSION AGENTS

[75] Inventor: John A. Jaecker, Homewood, Ill.

[73] Assignee: Atlantic Richfield Company, Los Angeles, Calif.

[21] Appl. No.: 802,300

[22] Filed: Jan. 2, 1986

Related U.S. Application Data

[62] Division of Ser. No. 601,136, Apr. 16, 1984, Pat. No. 4,568,785.

[51] Int. Cl.$^4$ .......................... B01J 21/14; B01J 23/18; B01J 23/14; B01J 23/34
[52] U.S. Cl. ................................. 502/241; 502/242; 502/243; 502/249; 502/251; 502/324; 502/340; 502/341
[58] Field of Search ............... 502/241, 324, 242, 243, 502/249, 251, 340, 341

[56] References Cited

U.S. PATENT DOCUMENTS

| | | | |
|---|---|---|---|
| 2,427,707 | 9/1947 | Brimm | 502/324 |
| 2,482,308 | 9/1949 | Wernlund | 502/324 |
| 3,392,125 | 7/1968 | Kelly et al. | 502/324 |
| 3,700,605 | 10/1972 | Dobman et al. | 502/324 |
| 3,715,322 | 2/1973 | Kobayashi et al. | 502/324 |

FOREIGN PATENT DOCUMENTS 71639  5/1982  Japan .................................. 502/241

*Primary Examiner*—Carl F. Dees
*Attorney, Agent, or Firm*—Craig E. Larson

[57] ABSTRACT

An improved support for a contact agent, useful for converting methane to higher hydrocarbon products by contacting a gas comprising methane with a contact agent at a selected temperature, is formed by sintering the surface of the support.

14 Claims, No Drawings

PREPARATIVE PROCESS FOR METHANE CONVERSION AGENTS

This is a division of application Ser. No. 601,136, filed Apr. 16, 1984, now U.S. Pat. No. 4,568,785.

FIELD OF THE INVENTION

This invention relates to the synthesis of hydrocarbons from a methane source. A particular application of this invention is a method for converting natural gas to more readily transportable material. More particularly, it relates to the improved preparation of reducible metal oxide compositions useful as catalysts in such applications.

DESCRIPTION OF THE PERTINENT ART

A major source of methane is natural gas. Other sources of methane have been considered for fuel supply (e.g., the methane present in coal deposits or formed during mining operations). Relatively small amounts of methane are also produced in various petroleum processes.

The composition of natural gas at the wellhead varies, but the major hydrocarbon present is methane. For example, the methane content of natural gas may vary within the range of about 40 to about 95 volume percent. Other constituents of natural gas include ethane, propane, butane, pentane (and heavier hydrocarbons), hydrogen sulfide, carbon dioxide, helium, and nitrogen.

Natural gas is classified as dry or wet, depending upon the amount of condensable hydrocarbons contained in it. Condensable hydrocarbons generally comprise $C_3+$ hydrocarbons, although some ethane may be included. Gas conditioning is required to alter the composition of wellhead gas; processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting and revaporizing natural gas are complex, energy intensive and require extensive safety precautions. Transport of natural gas has been a continuing problem in the exploitation of natural gas resources. It would be extremely valuable to be able to convert methane (e.g., natural gas) to more readily transportable products. Moreover, direct conversion to olefins such as ethylene or propylene would be extremely valuable to the chemical industry.

Recently, it has been discovered that methane may be converted to higher hydrocarbons by a process which comprises contacting methane with an oxidative synthesizing agent at synthesizing conditions (e.g., at a temperature selected within the range of about 500° to about 1000° C.). An oxidative synthesizing agent is a composition having as a principal component at least one oxide of at least one metal, which composition produces higher $C_2+$ hydrocarbon products, water and a composition comprising a reduced metal oxide when contacted with methane at synthesizing conditions. Reducible oxides of several metals have been identified which are capable of converting methane to higher hydrocarbons. In particular, oxides of manganese, tin, indium, germanium, lead, antimony and bismuth are most useful.

In particular useful compositions, the oxidative synthesizing agents are supported by magnesia or silica. These supports typically have a low resistance to attrition. Additionally, the particle density of the silica support is lower than desired for fluidization purposes.

Accordingly, an object of this invention is to provide an improved process for converting methane to higher hydrocarbons. A further object of this invention is an improved oxidative synthesizing agent with improved stability and resistance to attrition—an agent that maintains desirable conversion properties for longer periods of time.

Other aspects, objects and the several advantages of this invention will become apparent to those skilled in the art upon reading this Specification and the appended claims.

SUMMARY OF THE INVENTION

An improved hydrocarbon conversion process has been discovered which comprises contacting hydrocarbons, preferably a gas comprising methane, with a contact agent at conditions to convert the hydrocarbons, preferably at a temperature selected within the range of about 500° to about 1000° C., which agent comprises:
(a) at least one reducible oxide of at least one metal, which oxide is reduced and produces higher hydrocarbon products and water when contacted with methane at the selected temperature; and
(b) a support associated with the reducible oxide, the surface of at least a portion of the support being sintered at an elevated temperature, preferably to about 0.33 of the normal melting temperature of the material of the support.

This invention further relates to a novel process for the production of an improved contact agent which provides for sintering at least a portion of a support, admixing the sintered support with at least one metal, which forms at least one reducible oxide as defined herein.

DETAILED DESCRIPTION OF THE INVENTION

The contact agent of this invention is a composition comprising at least one reducible oxide of at least one metal and a support. The reducible oxide produces higher hydrocarbon products, water and a reduced metal oxide when contacted with methane at a temperature selected within the range of about 500° to 1000° C. The term "reducible" is used to identify those oxides of metals which are reduced by the methane contact. The term "oxide(s) of metal(s)" includes: (1) one or more metal oxides (i.e., compounds described by the general formula $M_xO_y$ wherein M is a metal, O is oxygen, and the subscripts x and y designate the relative atomic proportions of metal and oxide in the composition); and/or (2) one or more oxygen-containing metal compounds; provided that such oxides and compounds have the capability of performing to produce higher hydrocarbon products as set forth herein.

The preferred agents comprise reducible oxides of metals selected from the group consisting of manganese, tin, indium, germanium, antimony, lead, bismuth, and mixtures thereof. The particularly preferred agents comprise reducible oxides of manganese and mixtures of reducible oxides of manganese with other agents.

The agent is supported by or diluted with a support material such as silica, alumina, magnesia, titania, zirconia, and combinations thereof. Preferably, the support material is selected from a group consisting of magnesia, silica, and mixtures thereof. More preferably, the support material is magnesia. Moreover, the support material itself may comprise an alkali metal (e.g., suitable supports include sodium oxide, potassium oxide, etc.).

The support is preferably prepared in powdered form, more preferably having a particle size ranging from about 20 to about 200 microns, and still preferably about 100 microns. The support is dried to the extent that upon subsequent sintering the particles do not steam or explode. Preferably, the particles have a water content of less than about 1.0 weight percent water.

The support is sintered to an elevated temperature (i.e., heated to a high temperature without melting the support) by exposure for a short time to a temperature high enough to cause at least partial fusion of the surface of the particles. This exposure can occur before or after the addition of the metal which forms at least one reducible oxide (e.g., derived from sodium or lithium permanganate, or mixtures of manganese and sodium, or lithium salts). The elevated (sintering) temperature varies with the composition of the material being sintered. In one preferred embodiment, the elevated temperature is equal to about 0.33 of the normal melting temperature of the material of the support.

The exposure to the high temperature may be accomplished by allowing the particles to briefly contact a flame or a hot surface. Alternatively, a laser or other electromagnetic radiation source with a limited depth of surface penetration of the support may be used. The degree of surface sintering can be controlled by the temperature of the flame or of the hot surface, by the intensity of the light, or by the length of time of exposure.

The particles should be removed from the heat source quickly so that the effect of the sintering is confined to the depth desired. Removal from the flame or hot surface can be accomplished by several means—by transporting the particles out of the region of the hot substance, by cooling the hot substance with another material, by contacting the particles with a heat sink to remove the heat absorbed from the hot substance, or by combinations of these and other methods. When a laser is used, its light can be diverted or absorbed. Removal of heat by radiation or conduction is preferred.

The addition of steam or an inert gas (such as nitrogen) or a reactive gas (such as hydrogen chloride) is preferred to control the sintering process.

Preferred sintering temperatures for the support material are in the range of about 1690° to about 5070° F. for magnesia and about 1040° to about 3110° F. for silica. Sintering of the support may take place in a period of time in the range of about 0.5 to about 15 minutes or more, preferably in a period of time in the range of about 1 to about 10 minutes.

The method of the present invention preferably provides support compositions exhibiting a surface area ranging from about 30 to about 90 square meters per gram.

The preferred contact agent of this invention contains, in addition to the foregoing elements, at least one alkali metal. The atomic ratio in which these materials are combined to form the contact agent is not narrowly critical. However, the preferred atomic ratio of the reducible oxide component (expressed as the metal, e.g., Mn) to the alkali metal component (expressed as the metal, e.g., Na) is within the range of about 0.1:1 to about 100:1, more preferably within the range of about 0.3:1 to about 10:1.

The contact agent can be prepared by any suitable method. Conventional methods such as precipitation, coprecipitation, impregnation or granulation can be used. Supported solids may be prepared by methods such as adsorption, impregnation, precipitation, coprecipitation and granulation. Thus, a compound of manganese, tin, indium, germanium, antimony, lead, bismuth, and mixtures thereof, and the sintered support can be combined in any suitable way.

A suitable method of preparation is to impregnate a sintered support with solutions of compounds of the desired metals. Suitable metal compounds useful for impregnation include the acetates, acetylacetonates, oxides, carbides, carbonates, hydroxides, formates, oxalates, nitrates, phosphates, sulfates, sulfides, tartrates, fluorides, chlorides, bromides or iodides.

After impregnation, the resulting composite is dried in an oven to remove solvent and the dried solid is prepared for use by calcining at elevated temperatures in an oxygen-containing gas (e.g., air) prior to use in the process of the invention. Particular calcination temperatures will vary, depending upon the particular metal compound or compounds employed. Preferably, the air temperature is selected within the range of about 300° to about 1200° C.

In addition to methane, the preferred feedstock employed in the method of this invention may contain other hydrocarbon or non-hydrocarbon components, although the methane content should typically be within the range of about 40 to about 100 volume percent, preferably about 80 to about 100 volume percent, more preferably about 90 to about 100 volume percent.

Operating temperatures for contacting the methane with the contact agent are preferably selected within the range of about 500° to about 1000° C.; the particular temperature selected depending upon the particular reducible metal oxides employed in the contact agent. For example, reducible oxides of certain metals may require operating temperatures below the upper part of the recited range to minimize sublimation or volatilization of the metals (or compounds thereof) during methane contact. Examples include reducible oxides of indium, germanium or bismuth (operating temperatures will preferably not exceed about 850° C.)

Operating pressures for the methane contacting step are not critical to the presently claimed invention. However, both general system pressure and partial pressure of methane have been found to affect overall results. Preferred operating pressures are within the range of about 1 to about 30 atmospheres.

Contacting methane and a reducible metal oxide to form higher hydrocarbons from methane also produces reduced metal oxides and water. The exact nature of the reduced metal oxides is unknown, and so is referred to herein as "reduced metal oxides". Regeneration of reduced metal oxide is readily accomplished by contacting such reduced material with oxygen (e.g., an oxygen-containing gas such as air) at elevated temperatures, preferably at a temperature selected within the range of about 300° to about 1200° C.; the particular temperature selected depending on the metal(s) included in the contact agent.

In carrying out the present process, a single reactor apparatus containing a fixed bed of solids may be used with intermittent or pulsed flow of a first gas comprising methane followed by intermittent or pulsed flow of a second gas comprising oxygen (e.g., oxygen, oxygen diluted with an inert gas, or air, preferably air). The methane contacting step and the oxygen contacting step may also be performed in physically separate zones with solids recirculating between the two zones.

Thus, a suitable method for synthesizing hydrocarbons from a methane source comprises: (a) contacting a gas comprising methane and particles comprising a contact agent to form higher hydrocarbon products, water and reduced metal oxide; (b) removing particles comprising reduced metal oxide from the first zone and contacting the reduced particles in a second zone with an oxygen-containing gas to form particles comprising a contact agent; and (c) returning the particles produced in the second zone to the first zone. The steps are preferably repeated at least periodically, and more preferably the steps are continuous. In the more preferred embodiment, solids are continuously circulated between at least one methane contact zone and at least one oxygen contact zone.

Particles comprising a reducible metal oxide which are contacted with methane may be maintained as fluidized, ebullating, or entrained beds of solids. Preferably, methane is contacted with a fluidized bed of solids.

Similarly, particles comprising reduced metal oxide which are contacted with oxygen may be maintained as fluidized, ebullating, or entrained beds of solids. Preferably, oxygen is contacted with a fluidized bed of solids.

In the more preferred embodiment of the present invention, methane feedstock and particles comprising a contact agent are continuously introduced into a methane contact zone maintained at synthesizing conditions. Synthesizing conditions include the temperatures and pressures described above. Gaseous reaction products of the methane contact zone (separated from entrained solid) are further processed (e.g., passed through a fractionating system wherein the desired hydrocarbon products are separated from unconverted methane and combustion products). Unconverted methane may be recovered and recycled to the methane contact zone.

Particles comprising reduced metal oxide are contacted with oxygen in an oxygen contact zone for a time sufficient to oxidize at least a portion of the reduced oxide to produce a reducible metal oxide and to remove (i.e., combust) at least a portion of any carbonaceous deposit which may form on the particles in the methane contact zone. The conditions of the oxygen contact zone will preferably include a temperature selected within the range of about 300° to about 1200° C., pressures of up to about 30 atmospheres, and average particle contact time within the range of about 1 to about 120 minutes. Sufficient oxygen is preferably provided to oxidize all reduced metal oxide to produce a reducible oxide and to completely combust any carbonaceous deposit material deposited on the particles. At least a portion of the particles comprising the contact agent which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady-state operation of the synthesizing system.

What is claimed is:

1. A method for preparing a contact agent comprising:
   (a) at least one reducible oxide of at least one metal, which oxide is reduced and produces higher hydrocarbon products and water when contacted with methane at a selected temperature in the range of about 500° to about 1000° C.; and
   (b) a support associated with said reducible oxide; which method comprises:
      (i) sintering the surface of at least a portion of a support selected from the group consisting of magnesia, silica, and mixtures thereof;
      (ii) combining said support with at least one metal which forms at least one of said reducible oxides; and
      (iii) calcining said combined support and metal.

2. The method of claim 1 wherein said sintering comprises heating said support to about 0.33 of the normal melting temperature of the material of said support.

3. The method of claim 1 wherein said support comprises magnesia and is sintered at a temperature of about 1690° and about 5070° F.

4. The method of claim 1 wherein said support comprises silica and is sintered at a temperature of about 1040° and about 3110° F.

5. The method of claim 1 wherein said reducible oxide is selected from the group consisting of manganese, tin, indium, germanium, antimony, lead, bismuth, and mixtures thereof.

6. The method of claim 1 wherein said agent comprises additionally a promoting amount of at least one promoter selected from the group consisting of alkali metals and compounds thereof.

7. The method of claim 1 wherein the surface area of said support ranges from about 30 to about 90 square meters per gram.

8. In an improved composition of matter comprising:
   (a) at least one reducible oxide of at least one metal, which oxide is reduced and produces higher hydrocarbon products and water when contacted with methane at a selected temperature in the range of about 500° to about 1000° C. and
   (b) a support associated with said oxide, the improvement which comprises employing as the support a material selected from the group consisting of magnesia, silica and mixtures thereof, the surface of at least a portion of said support being sintered.

9. The composition of claim 8 wherein said sintering comprises heating said support to about 0.33 of the normal melting temperature of the material of said support.

10. The composition of claim 8 wherein said support comprises magnesia and is sintered at a temperature of about 1690° and about 5070° F.

11. The method of claim 8 wherein said support comprises silica and is sintered at a temperature of about 1040° and about 3110° F.

12. The composition of claim 8 wherein said reducible oxide is selected from the group consisting of manganese, tin, indium, germanium, antimony, lead, bismuth, and mixtures thereof.

13. The composition of claim 8 wherein said agent comprises additionally a promoting amount of at least one promoter selected from the group consisting of alkali metals and compounds thereof.

14. The composition of claim 8 wherein the surface area of said support ranges from about 30 to about 90 square meters per gram.

* * * * *